(12) United States Patent
Kuster

(10) Patent No.: US 9,968,390 B2
(45) Date of Patent: May 15, 2018

(54) BONE FIXING APPARATUS

(75) Inventor: Markus Kuster, Mosman Park (AU)

(73) Assignee: ZIMMER GMBH, Winterthur (CH)

( * ) Notice: Subject to any disclaimer, the term of this patent is extended or adjusted under 35 U.S.C. 154(b) by 326 days.

(21) Appl. No.: 14/343,643

(22) PCT Filed: Sep. 14, 2012

(86) PCT No.: PCT/EP2012/068065
§ 371 (c)(1),
(2), (4) Date: Mar. 28, 2014

(87) PCT Pub. No.: WO2013/037939
PCT Pub. Date: Mar. 21, 2013

(65) Prior Publication Data
US 2014/0222086 A1    Aug. 7, 2014

(30) Foreign Application Priority Data
Sep. 14, 2011  (EP) ..................................... 11007513

(51) Int. Cl.
*A61B 17/80*   (2006.01)
*A61B 17/70*   (2006.01)

(52) U.S. Cl.
CPC ...... *A61B 17/8047* (2013.01); *A61B 17/7059* (2013.01)

(58) Field of Classification Search
CPC ............................ A61B 17/80; A61B 17/8047
(Continued)

(56) References Cited

U.S. PATENT DOCUMENTS 5,607,426 A * 3/1997 Ralph ................ A61B 17/7037
606/287
5,904,683 A * 5/1999 Pohndorf ........... A61B 17/7059
606/287
(Continued)

FOREIGN PATENT DOCUMENTS

CN      1582132 A     2/2005
CN    101106949 A     1/2008
(Continued)

OTHER PUBLICATIONS

"International Application Serial No. PCT/EP2012/068065, International Preliminary Report on Patentability dated Mar. 20, 2014", (English Translation), 8 pgs.
(Continued)

*Primary Examiner* — Christopher Beccia
(74) *Attorney, Agent, or Firm* — Schwegman Lundberg & Woessner, P.A.

(57) ABSTRACT

An implantable device is described, comprising an implant (12), wherein the implant comprises at least one opening (22), at least one anchoring element (14) for fixing the implant to at least one bone, wherein the respective anchoring element comprises a shank (20) and a head (18) and wherein at least a part of the shank can be guided through the respective opening while the head can be seated in the respective opening, and a locking mechanism with a fixation element (16) and a radially deformable annular element (26) that can be pressed against the head of the anchoring element by actuation of the fixation element, in order to fix the head in the opening of the implant. The opening of the implant has a recess (28) having a support surface (24) for the head of the anchoring element.

20 Claims, 2 Drawing Sheets

Figure 1:
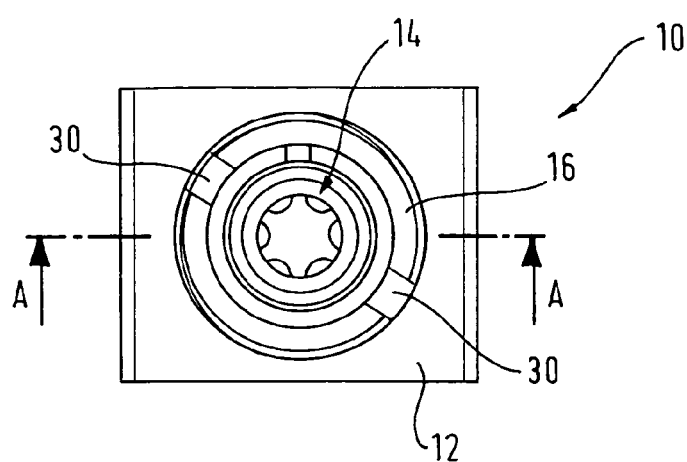

(58) Field of Classification Search
USPC .................. 606/70, 71, 280–299, 300–331
See application file for complete search history.

(56) References Cited

U.S. PATENT DOCUMENTS

| | | | | |
|---|---|---|---|---|
| 6,022,350 | A | * | 2/2000 | Ganem .............. A61B 17/7059 606/272 |
| 7,524,325 | B2 | * | 4/2009 | Khalili ............... A61B 17/7059 606/290 |
| 7,635,364 | B2 | | 12/2009 | Barrall et al. |
| 8,486,118 | B2 | | 7/2013 | Mathieu et al. |
| 2004/0087951 | A1 | | 5/2004 | Khalili |
| 2012/0059425 | A1 | * | 3/2012 | Biedermann ...... A61B 17/8042 606/291 |

FOREIGN PATENT DOCUMENTS

| | | |
|---|---|---|
| DE | 60203942 T2 | 5/2006 |
| EP | 0828459 B1 | 9/2003 |
| EP | 1520561 B1 | 1/2010 |
| WO | WO-9909903 A1 | 3/1999 |
| WO | WO-2008119006 A1 | 10/2008 |
| WO | WO-2009043827 A1 | 4/2009 |
| WO | WO-2013037939 A1 | 3/2013 |

OTHER PUBLICATIONS

"International Application Serial No. PCT/EP2012/068065, International Preliminary Report on Patentability dated Aug. 22, 2013 with Demand filed Jul. 11, 2013", (W/ English Translation), 29 pgs.

"International Application Serial No. PCT/EP2012/068065, Search Report dated Dec. 5, 2012", 5 pgs.

"International Application Serial No. PCT/EP2012/068065, Written Opinion dated Dec. 5, 2012", 5 pgs.

* cited by examiner

BONE FIXING APPARATUS

PRIORITY APPLICATION

This application is a U.S. National Stage Application under 35 U.S.C. 371 from International Application No. PCT/EP2012/068065, filed Sep. 14, 2012, and published as WO 2013/037939 A1 on Mar. 21, 2013, which claims the benefit of priority of European Patent Application Serial No. 11007513.2, filed Sep. 14, 2011, the benefit of priority of each of which is claimed hereby, and each of which are incorporated by reference herein in its entirety.

The present invention relates to an implantable apparatus.

For example, for treating a bone fracture the fracture is fixed in its correct position (reposition) after aligning the individual bone fragments by means of pins, screws, wires or plates. A plate can in particular be used for the fixing which is fastened to the individual bone fragments by means of anchorage elements, in particular bone screws. In this kind of treatment, a compression effect is achieved such that the individual bone fragments are held in a fixed position with respect to one another and are pressed toward one another by the plate and by the screws. The implanted apparatus can, however, also e.g. be used for stiffening a spinal column segment, in particular for fastening a plate between two vertebrae, or for fastening a joint replacement such as a hip implant or a shoulder implant.

The document U.S. Pat. No. 5,904,683 A describes an implantable apparatus having locking caps to lock polyaxial bone screws in a plate in a stable angle manner. The document EP 0 828 459 B1 likewise shows an implantable apparatus in which an annular insert is additionally provided to fix the respective polyaxial bone screw in a plate with spatial stability.

The implantable apparatus comprises an implant which has at least one opening. The implantable apparatus is in particular a bone fixing apparatus, in particular for the surgical care of fractures. The implant is in particular a fixing element, in particular a fracture fixing plate.

The implantable apparatus furthermore comprises at least one anchorage element for fastening the implant to at least one bone. The respective anchorage element comprises a shank and a head, wherein at least one part of the shank can be led through the respective opening, while the head can be supported in the respective opening.

The implantable apparatus additionally has a locking mechanism with a lock element and a radially deformable ring element which can be pressed toward the head of the anchorage element by actuating the lock element to fix the anchorage element in the opening of the implant.

The opening of the implant has a recess which has a support surface for the head of the anchorage element, in particular such that the head contacts the support surface in an assembled state of the implantable apparatus. In particular only the ring element and the lock element cooperate directly on the assembly of the implantable apparatus such that the ring element is radially compressed. The recess is formed at a proximal side of the implant. The recess is in particular a depression. The proximal side is to be understood as the side of the implant facing the surgeon during the surgery; a distal side is the side remote from the surgeon.

A low construction height of the implant can be achieved by the integration of the locking mechanism into the implant. The anchorage element and the lock element can be at least partly decoupled from one another with respect to the rotary movement on the tightening of the lock element by the additional use of the ring element. Since the head lies directly on the implant, in particular not indirectly via the ring element, a rotation of the support surface relative to the head can be prevented on the tightening of the lock element. This allows a reliable locking of the anchorage element or elements in the implant.

In an embodiment, the implant and the head of the anchorage element are configured for the polyaxial support of the anchorage element in the respective opening of the implant. The anchorage apparatus is in particular configured such that an angular position of the anchorage element is freely settable within a predefined range relative to an axis of the opening or to the implant before fixing the head in the opening.

In a further embodiment, the ring element is arranged between the lock element and the head of the anchorage element in an assembled state of the implanted apparatus. The ring element can be arranged around a section of the head of the anchorage element of spherical design in a mounted state of the implantable apparatus. The ring element and/or the lock element is/are in particular arranged radially from and/or concentric to the head.

In a further embodiment, the ring element is a slit ring. Alternatively or additionally, the ring element can be radially elastically compressible and/or squeezable, in particular by the lock element. The ring element can be acted on by a radial force by the lock element.

In an exemplary embodiment, a radially external geometry of the ring elements is configured as conical at least sectionally, with an opening angle of the conical section in particular amounting to 1° to 12°, in particular to 2° to 8°. A conical configuration can be described by the geometry of a jacket of a truncated cone. The opening angle is to be understood as twice the value of an angle between a surface line of the truncated cone and its axis of rotation.

In a further embodiment, a radially internal geometry of the lock element is configured as conical at least sectionally, with an opening angle of the conical section amounting to 1° to 12°, in particular to 2° to 8°. The internal geometry of the lock element is in particular configured complementary to the external geometry of the ring element.

It is sufficient in this respect if at least one of the two geometries, i.e. either the radially external geometry of the ring element or the radially internal geometry of the lock element is configured as conical at least sectionally. Both geometries are preferably configured as conical at least sectionally. The two conical sections are in particular configured complementary to one another.

In an embodiment, the respective conical section of the ring element and/or of the lock element tapers against an introduction direction of the anchorage element. The anchorage element is introduced from proximal to distal into the implant or into the opening formed therein. The introduction direction accordingly faces from the proximal side of the implant to the distal side of the implant. In the implanted state of the implantable apparatus, the head of the anchorage element faces in the proximal direction; a tip of the anchorage element faces in the distal direction.

In a further embodiment, a radial inner side of the ring element cooperating with the head of the anchorage element and/or at least one section of the head cooperating with the ring element is surface treated, in particular roughened, in order to increase a friction acting between the head and the ring element.

In a further embodiment, the lock element can be screwed into the opening of the implant, in particular into the recess of the opening of the implant.

The anchorage element is in particular a polyaxial screw.

In a further embodiment, the recess of the opening has a concave support surface for the head of the anchorage element. Alternatively or additionally, the head of the anchorage element is of spherical design at the end facing the shank such that the anchorage element can be variably positioned with respect to its angular position relative to the implant before a fixing.

In an embodiment, the complete shank of the anchorage element, but not the head of the anchorage element, can be led through the opening of the implant, with in particular the dimensions of the head and of the opening being coordinated with one another such that the head cannot be led through the opening.

In a further embodiment, the lock element is a ring nut.

In an embodiment one or more slopes, which act, in particular cooperate, on the assembly of the implantable apparatus such that the ring element is radially compressed, are formed only at the ring element and/or at the lock element.

The different embodiments of an implantable apparatus stated in accordance with the independent claim directed to the implantable apparatus or the features realized there can naturally be combined with one another.

Figure 2:
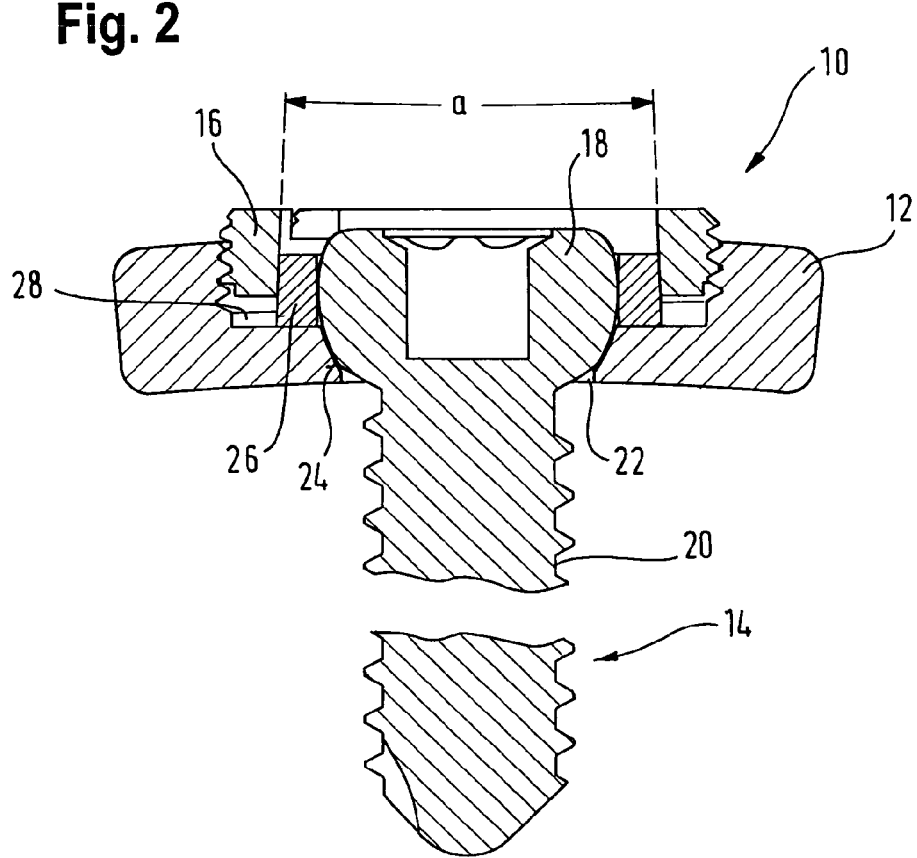
Figure 3:
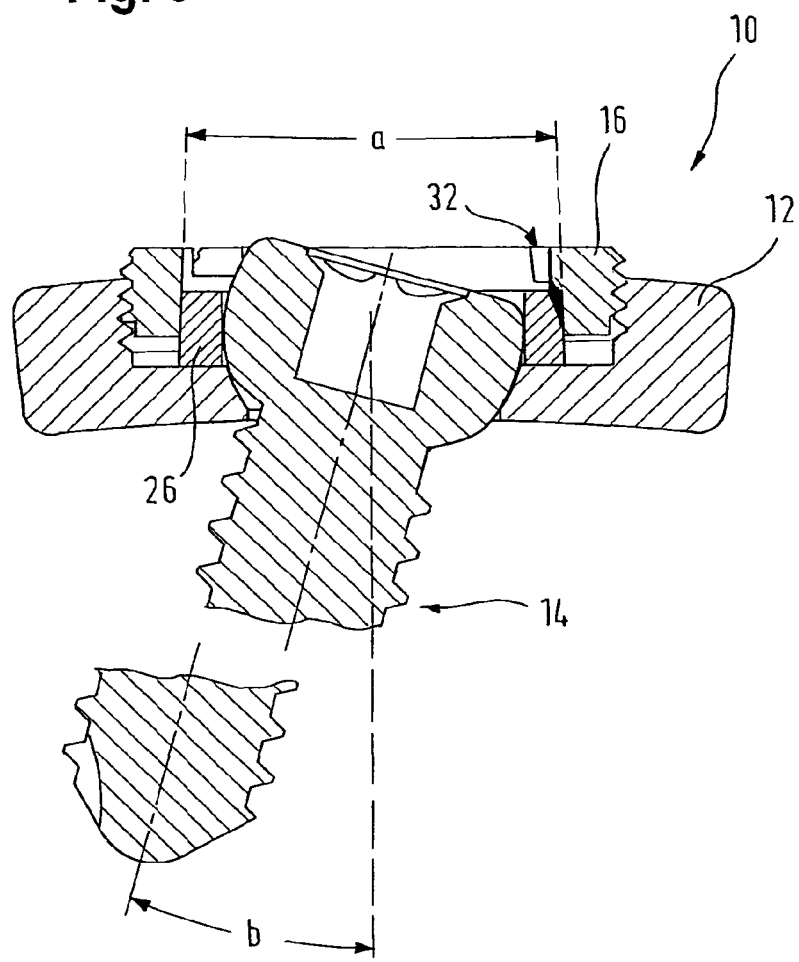

The invention will be explained in more detail in the following with reference to embodiments illustrated in the drawings. In this respect, the embodiments and the drawings should only be understood in an instructive manner and should not serve for the restriction of the subjects described in the claims. The representations have been simplified in the drawings; details not necessary for the understanding of the invention have been omitted. The drawings show:

FIG. 1 a plan view of a section of a bone fixing apparatus in accordance with an embodiment; and FIGS. 2 and 3 a cross-section through the embodiment shown in FIG. 1 in different states.

FIG. 1 shows a bone fixing apparatus 10 having an elongate fracture fixing plate 12, which is, however, only shown sectionally, and having a bone screw 14 which is led through an opening 22 of the plate 12. Beside the shown opening 22, the plate 12 has at least one further opening through which a respective further bone screw can be led. Further openings and/or bone screws can be configured analog to the shown opening 22 or bone screw 14.

The bone screw 14 can be fastened to a bone of a patient by means of a suitable tool to fix the plate 12 to the bone. The bone screw 14 is a so-called polyaxial screw which can be reliably connected to the plate 12 within a predefined angular region in the suitable angular position relative to the plate 12. A locking mechanism having a ring nut 16 is provided for the locking of the screw 14 in the plate 12 at a stable angle. Analog locking mechanisms can be provided for further openings and/or bone screws.

To illustrate the operation of the locking mechanism for locking the screw 14 at the plate 12, a respective cross-section through the bone fixing apparatus 10 along the sectional plane A-A of FIG. 1 is shown in FIGS. 2 and 3

It can be recognized with respect to FIG. 2 that the screw 14 has a spherically formed head 18 and a shank 20 provided with an external thread. To fasten the plate 12 to a bone, the screw 14 is inserted through the opening 22 of the plate 12 and is screwed into the bone until the head 18 contacts a concave support surface 24 of the opening 22. The bone screw 14 can be fastened to the plate 12 at different angles relative to the plate 12 by the spherical design of the head 18 and of the corresponding shape of the contact surface 24. At this time, the screw 14 is already reliably anchored in the bone and only subsequently and independently thereof does the locking of the screw 14 to the plate 12 take place with the aid of the locking mechanism.

The locking mechanism comprises the ring nut 16 already mentioned above and a ring 26. Once the bone screw 14 has been screwed into the bone, the head 18 contacts the support surface 24 of the opening 22. The ring 26, which projects into a recess 28 of the opening 22, contacts the still exposed part of the head 18. The ring 26 is in particular a slit ring which has a little play with respect to the head 18 in a relaxed state or which only lightly contacts it such that the head 18 of the bone screw 14 can still be moved, in particular rotated or pivoted. The recess 28 has an internal thread so that the ring nut 16 provided with an external thread can be screwed into the recess 28 of the opening 22. The ring 26 is radially compressed by the screwing in of the ring nut 16, which is achieved in that the ring 26 has a conical external geometry and/or that the ring nut 16 has a conical internal geometry. In other words, its radial outer surface substantially corresponds to a jacket surface of a truncated cone which tapers in a direction away from the bone. An opening angle a of the truncated cone amounts to 5°, for example, with the opening angle to be understood as twice the angle between an axis of rotation of the truncated cone and a surface line. The ring nut 16 in the embodiment has a complementary internal geometry which makes it possible to lead the ring nut 16 a little beyond the conical outer side of the ring 26 and which, on the other hand, ensures that the inner side of the ring nut 16 comes into contact with the outer side of the ring 26 with an axial pushing over one another. When the ring nut 16 is turned in, the ring 26 is in particular compressed in the radial direction so that the inner side of the ring 26 is pressed toward the head 18 of the screw 14. The deformation of the ring 26 is elastic so that the ring 26 substantially adopts its original shape again on removal of the ring nut 16. This can also be achieved by the choice of a suitable material for the ring 26. In specific cases, a plastic deformation of the ring 26—possibly also only a partial deformation—can be provided.

Ultimately, the head 18 of the screw 14 is acted on by a force by the ring nut 16 via the ring 26 to fix the screw 14 at a stable angle relative to the plate 12. This force is effected by the turning in of the ring nut 16. To facilitate the turning in, the ring nut 16 has tool engagement parts, for example two radially extending slits 30 which are shown in FIG. 1. The operation of the locking mechanism is thus essentially based on converting an axially acting force, which is produced by a turning in of the ring nut 16 and by a suitable design of the internal geometry of the ring nut 16 and the external geometry of the ring 26, into force acting radially inwardly onto the head 18. In order to increase the friction between the ring 26 and the section of the head 18 cooperating with its inner side, the inner side of the ring and/or the screw head is roughened.

FIG. 3 shows the bone fixing apparatus 10 in a somewhat different situation than in FIG. 2. The bone screw 14 does not extend substantially perpendicular to the plate 12, but is rather tilted by an angle b. The locking mechanism described in detail above nevertheless allows a reliable spatially fixed fixing of the screw 14 to the plate 12.

In general, the total internal geometry of the ring 16 or the total external geometry of the ring 26 does not have to correspond to the jacket surface of a single cone. In other embodiments, inter alia a combination of a cylinder jacket surface with a cone or the combination of two truncated cones with different opening angles is also conceivable, for example.

The described embodiment have the common feature that the axial movement of the ring nut 16 is converted into a compression, in particular an elastic compression, of the ring 26 which is pressed toward the head 18. In this respect, the internal geometry of the ring 26 at least partly matches the shape of the head 18 to produce an active surface which is as large as possible between the ring 26 and the head 18. The head 18 is thus reliably connected to the ring 26 which is in turn secured by the ring nut 16.

The bone fixing apparatus 10 can be preassembled. For this purpose, the ring 26 and the ring nut 16 are already inserted into the recess 28 of the fracture fixing plate 12 before the fastening of the fracture fixing plate 12 to a bone or before the introduction of the bone screw 14 into the recess 28. The shank 20 and the head 18 of the anchorage element 14 can be led through an opening of the ring-shaped lock element 16. The screw head 18 can then be pressed into the ring—in particular on a radial expansion of the ring 26. To prevent the ring 26 from falling out of the preassembled bone fixing apparatus 10, a corresponding securing feature 32 is provided. The implantable apparatus can also be used in other areas than for the surgical care of fractures. The implant can, for example, also be configured as a hip shell or as a spinal column plate.

In view of the statements made here, further embodiments of the invention characterized in the claims become clear to the person skilled in the art which cannot be shown conclusively here.

All indications of alignment, positioning, orientation and direction which are used as required in the claims, in the description and in the drawings in connection with the implantable apparatus and in accordance with the technically usual conventions and which in particular relate to anatomical axes, planes, directions in space and directions of movement are familiar to the person skilled in the art and relate to the implanted state of the implanted apparatus.

REFERENCE NUMERAL LIST

10 bone fixing apparatus
12 fracture fixing plate
14 bone screw
16 ring nut
18 head
20 shank
22 opening
24 support surface
26 ring
28 recess
30 slit
32 securing feature
A-A sectional plane
a opening angle
b angle

The invention claimed is:

1. An implantable apparatus, comprising an implant, wherein the implant has at least one opening;
at least one anchorage element for fastening the implant to at least one bone, wherein the respective anchorage element comprises a shank and a head, and wherein at least a part of the shank can be led through the respective opening, while the head can be supported in the respective opening; and
a locking mechanism having a lock element with an internal conical surface and a radially deformable ring element with an external conical surface complementary to the internal conical surface of the lock element, wherein during assembly the ring element can be pressed toward the head of the anchorage element by actuating the lock element downwards relative to the ring element to fix the head in the opening of the implant, the external conical surface of the ring element being structured such that a diameter of the ring element decreases as the lock element is actuated downwards relative to the ring element;
wherein the opening of the implant has a recess which has a support surface that is contacted by the head of the anchorage element in an assembled state of the implantable apparatus, with only the ring element and the lock element cooperating directly on the assembly of the implantable apparatus such that the ring element is radially compressed.

2. The implantable apparatus in accordance with claim 1, wherein the implant and the head of the anchorage element are configured for the polyaxial support of the anchorage element in the respective opening of the implant.

3. The implantable apparatus in accordance with claim 1, wherein the ring element is arranged between the lock element and the head of the anchorage element and/or around a spherically designed section of the head of the anchorage element in an assembled state of the implantable apparatus.

4. The implantable apparatus in accordance with claim 1, wherein the ring element is a slit ring; and/or in that the ring element is radially elastically compressible.

5. The implantable apparatus in accordance with claim 1, wherein the external conical surface of the ring element defines an opening angle in a range of 1° to 12°.

6. The implantable apparatus in accordance with claim 5, wherein the internal conical surface of the lock element defines an opening angle in a range of 1° to 12°.

7. The implantable apparatus in accordance with claim 6, wherein the opening angle of the ring element is the same as the opening angle of the lock element.

8. The implantable apparatus in accordance with claim 7, wherein the respective conical surfaces taper against an introduction direction of the anchorage element.

9. The implantable apparatus in accordance with claim 1, wherein a radial inner side of the ring element cooperating with the head of the anchorage element and/or at least one section of the head cooperating with the ring element is/are surface treated, in particular roughened, in order to increase a friction acting between the head and the ring element.

10. The implantable apparatus in accordance with claim 1, wherein the lock element can be screwed into the recess of the opening of the implant.

11. The implantable apparatus in accordance with claim 1, wherein the recess of the opening has a concave support surface for the head of the anchorage element; and/or in that the head of the anchorage element is spherically designed at the end facing the shank such that the anchorage element can be variably positioned with respect to its angular position relative to the implant before a fixing.

12. The implantable apparatus in accordance with claim 1, wherein the complete shank of the anchorage element, but not the head of the anchorage element, can be led through the opening of the implant, with in particular the dimensions of the head and of the opening being coordinated with one another such that the head cannot be led through the opening.

13. The implantable apparatus in accordance with claim 1, wherein the lock element is a ring nut.

14. The implantable apparatus in accordance with claim 1, wherein one or more slopes, which act during the assembly of the implantable apparatus such that the ring element is radially compressed, are only formed at the ring element and/or at the lock element.

15. The implantable apparatus in accordance with claim 1, wherein the recess is formed at a proximal side of the implant.

16. The implantable apparatus in accordance with claim 8, wherein the introduction direction of the anchorage element is directed from a proximal side to a distal side of the implant.

17. The implantable apparatus in accordance with claim 1, wherein the implantable apparatus is a bone fixing apparatus, in particular for the surgical care of fractures.

18. The implantable apparatus in accordance with claim 1, wherein the implant is a fixing element, in particular a fracture fixing plate.

19. The implantable apparatus in accordance with claim 1, wherein the ring element and/or the lock element is/are arranged radially from and/or concentric to the head.

20. An implantable apparatus, comprising an implant, wherein the implant has at least one opening;
   at least one anchorage element for fastening the implant to at least one bone, wherein the respective anchorage element comprises a shank and a spherical head, and wherein at least a part of the shank can be led through the respective opening, while the spherical head can be supported in the respective opening; and
   a locking mechanism having an externally threaded lock element and a radially deformable slit ring element which can be pressed toward the spherical head of the anchorage element by actuating the externally threaded lock element downwards relative to the slit ring element to fix the spherical head in the opening of the implant, the slit ring element being structured such that a diameter of the slit ring element decreases as the externally threaded lock element is actuated downwards relative to the slit ring element;
   wherein the opening of the implant has a recess which has a support surface that is contacted by the spherical head of the anchorage element in an assembled state of the implantable apparatus, with only the slit ring element and the externally threaded lock element cooperating directly on the assembly of the implantable apparatus such that the slit ring element is radially compressed.

* * * * *